US008431375B2

(12) United States Patent
Happe et al.

(10) Patent No.: US 8,431,375 B2
(45) Date of Patent: Apr. 30, 2013

(54) METHOD FOR MARKING MATERIALS

(75) Inventors: Randolph Peter Happe, Zaandam (NL); Ronald Tako Marinus Van Den Dool, Culemborg (NL); Johannes Wilhelmus Timmermans, Ede (NL); Johannes Wilhelmus Leonardus Boumans, Maarn (NL)

(73) Assignee: Nederlandse Organisatie voor Toegepast-Natuurwetenschappelijk Onderzoek TNO, Delft (NL)

( * ) Notice: Subject to any disclaimer, the term of this patent is extended or adjusted under 35 U.S.C. 154(b) by 305 days.

(21) Appl. No.: 12/667,963

(22) PCT Filed: Jul. 4, 2008

(86) PCT No.: PCT/NL2008/050453

§ 371 (c)(1),
(2), (4) Date: Nov. 8, 2010

(87) PCT Pub. No.: WO2009/008716

PCT Pub. Date: Jan. 15, 2009

(65) Prior Publication Data

US 2011/0129865 A1 Jun. 2, 2011

(30) Foreign Application Priority Data

Jul. 6, 2007 (EP) .................................... 07112000

(51) Int. Cl.

| | |
|---|---|
| ***C12N 11/10*** | (2006.01) |
| ***C12N 9/30*** | (2006.01) |
| ***C12N 5/04*** | (2006.01) |
| *C12P 1/00* | (2006.01) |
| *C12Q 1/25* | (2006.01) |
| *C12Q 1/28* | (2006.01) |

(52) U.S. Cl.
USPC ................ 435/174; 435/29; 435/41; 435/410

(58) Field of Classification Search .................... 435/29, 435/41, 174, 410
See application file for complete search history.

(56) References Cited

U.S. PATENT DOCUMENTS

2007/0092480 A1 * 4/2007 Thijssen et al. ............ 424/78.09

FOREIGN PATENT DOCUMENTS

| | | |
|---|---|---|
| WO | 90/14441 | 11/1990 |
| WO | 00/64492 | 11/2000 |
| WO | 01/46334 | 6/2001 |
| WO | 03/048726 | 6/2003 |
| WO | 2004/105485 | 12/2004 |

OTHER PUBLICATIONS

Zherdev et al. 1999. Laccase from *Coriolus hirsutus* as Alternate Label for Enzyme immunoassay. Applied Biochemistry and Biotechnology, vol. 76, pp. 203-215.*
Zoreh Khani, et al., Alginate/Carbon Composite Beads for Laccase . . . , Biotechnol Letter, vol. 28, pp. 1779-1786, 2006.
Valentina Iannuccelli, et al., Effect of the Loading Method on the Drug Release . . . , Journal of Controlled Release, vol. 23, pp. 13-20, 1993.

* cited by examiner

*Primary Examiner* — Jon P Weber
*Assistant Examiner* — Kailash C Srivastava
(74) *Attorney, Agent, or Firm* — Lucas & Mercanti, LLP

(57) ABSTRACT

The invention relates to a marking system for marking objects wherein said system comprises a microparticle comprising a cross-linked polymer and a marker component wherein the release of said marker component is triggered by contact of the microparticle with an external stimulus and wherein said polymer is a carbohydrate or a protein.

10 Claims, 16 Drawing Sheets

Coated mung beans Uncoated mung beans

Coated grass seeds Uncoated grass seeds

Figure 11:
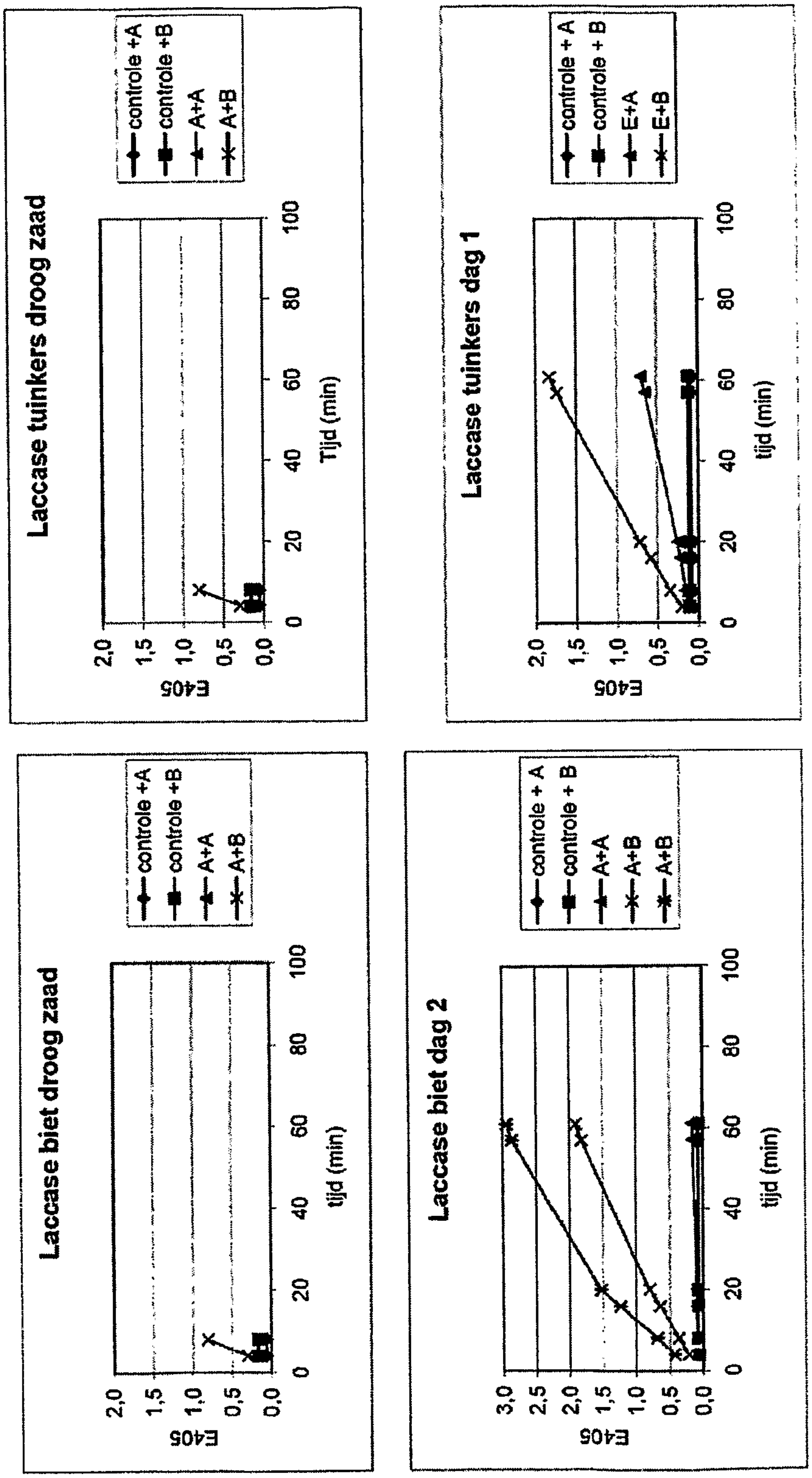

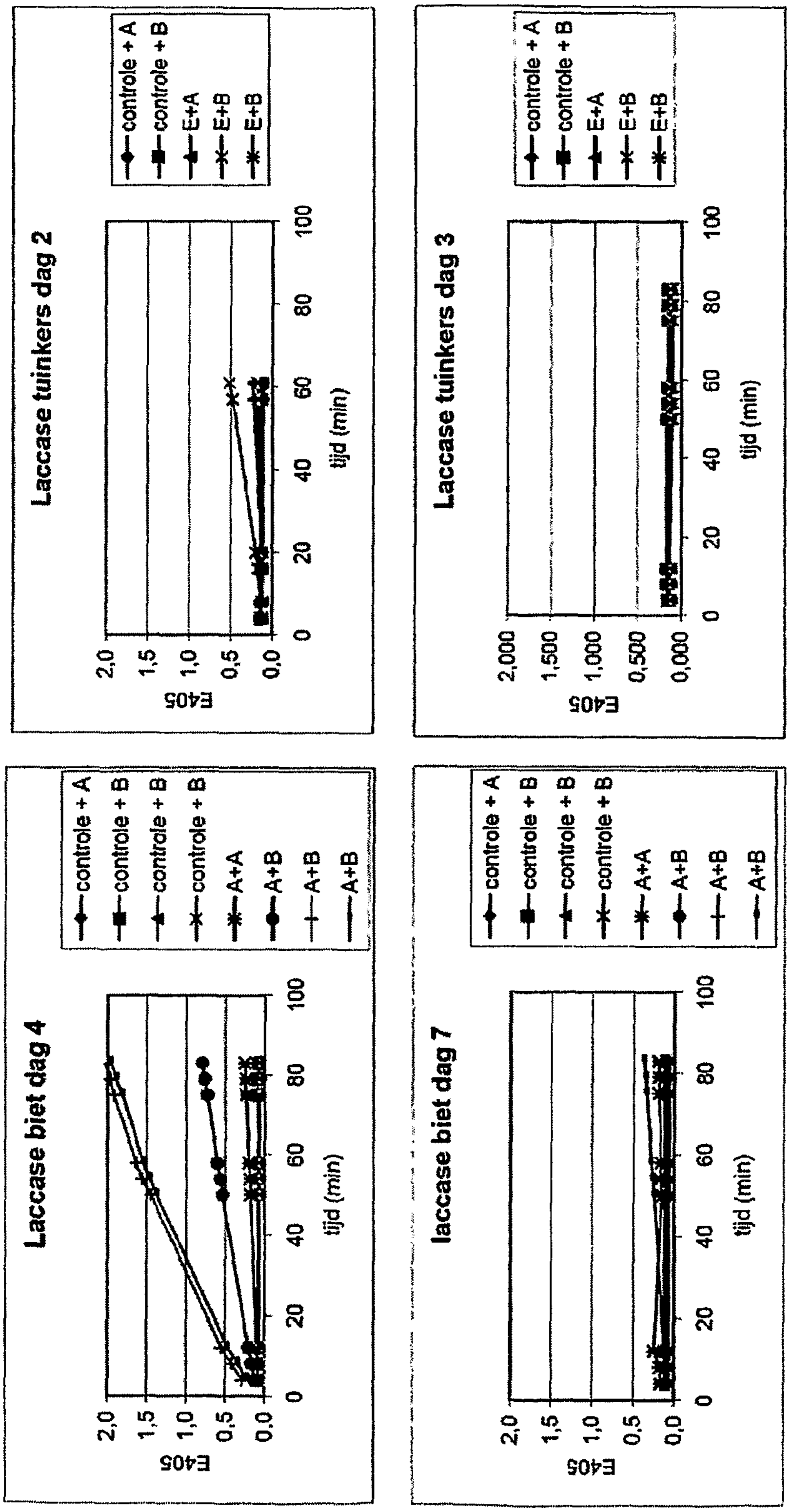
Fig. 11, contd.

Figure 12:
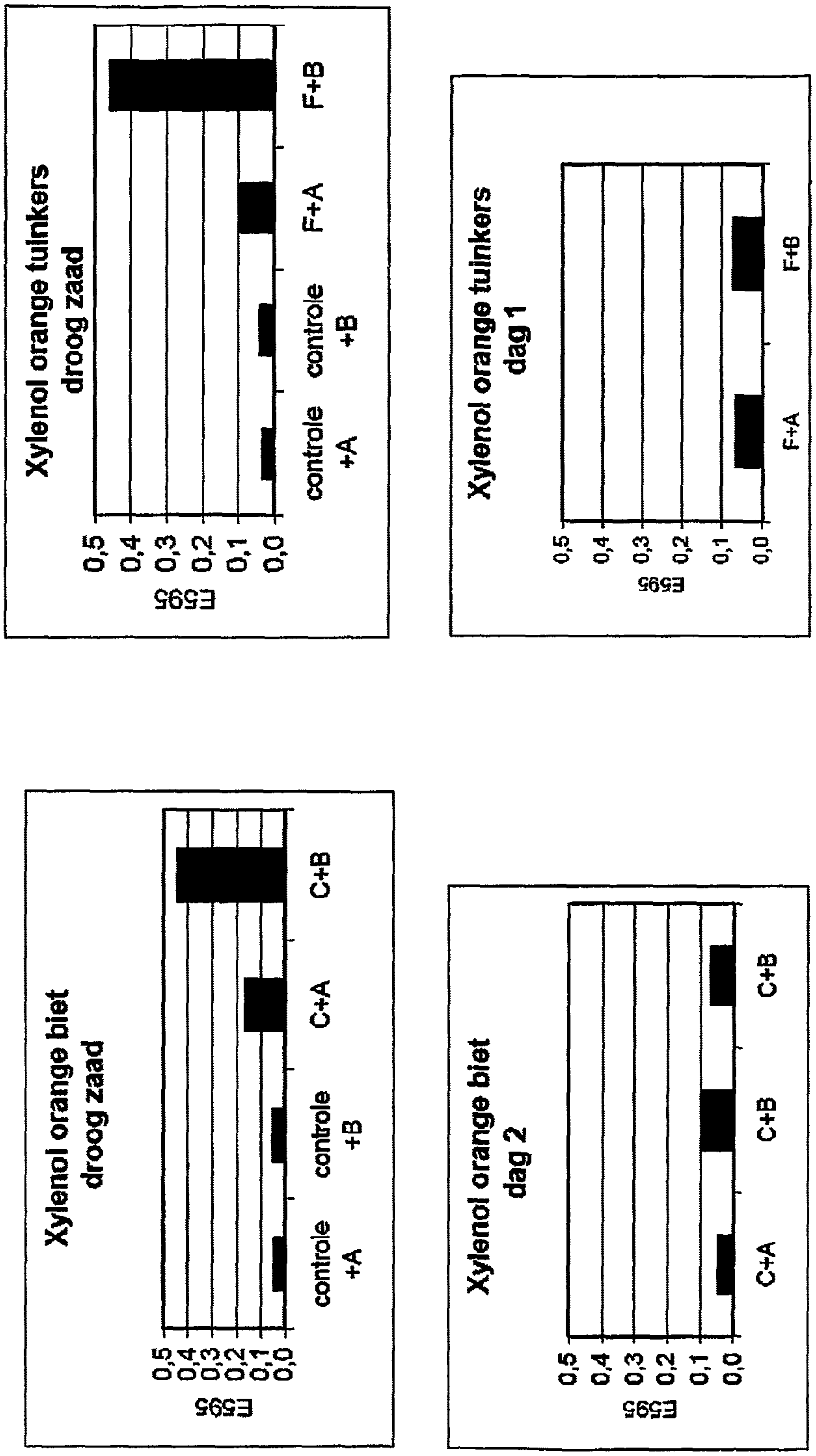

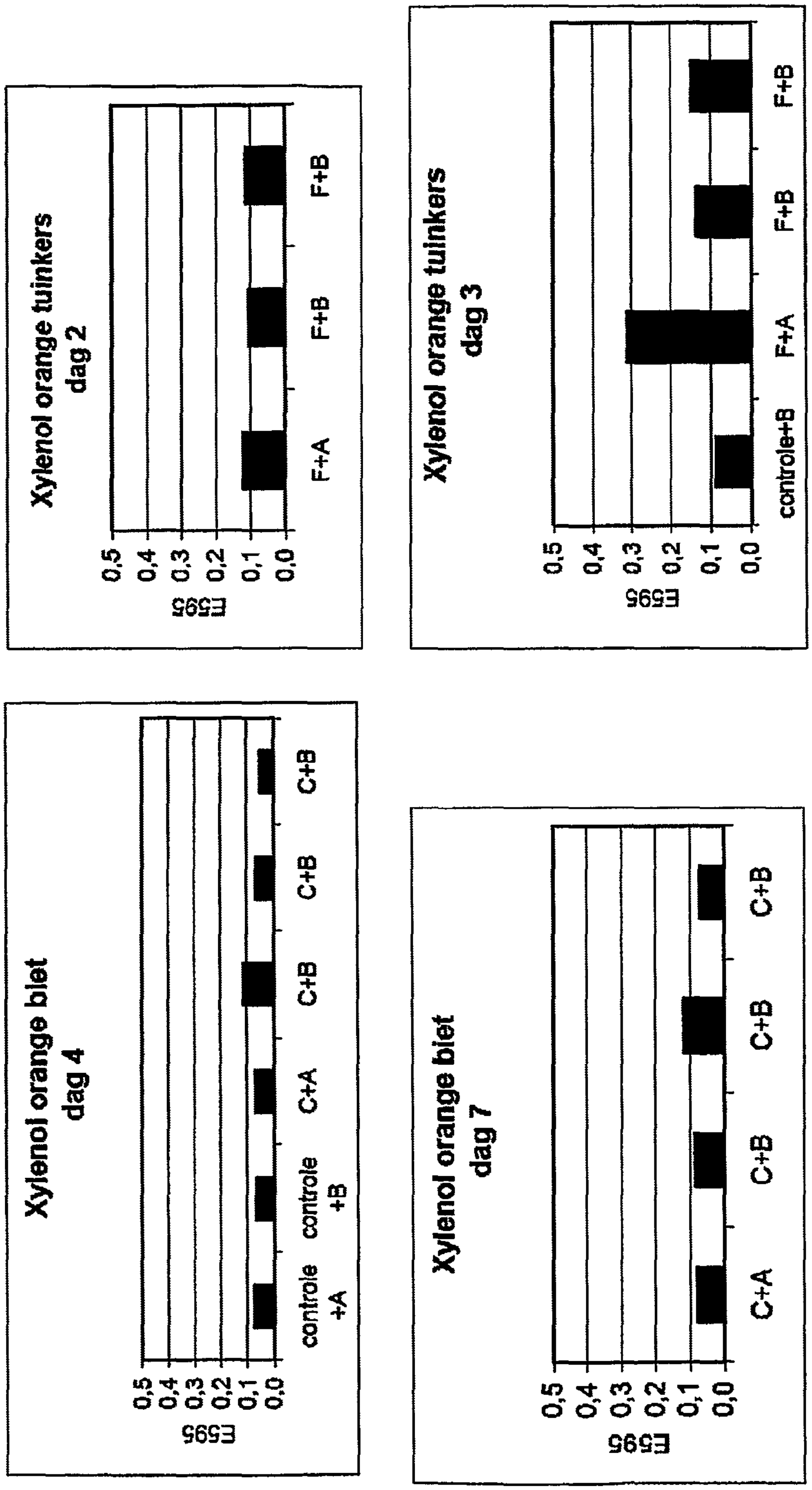
Fig. 12, contd.

Figure 13:
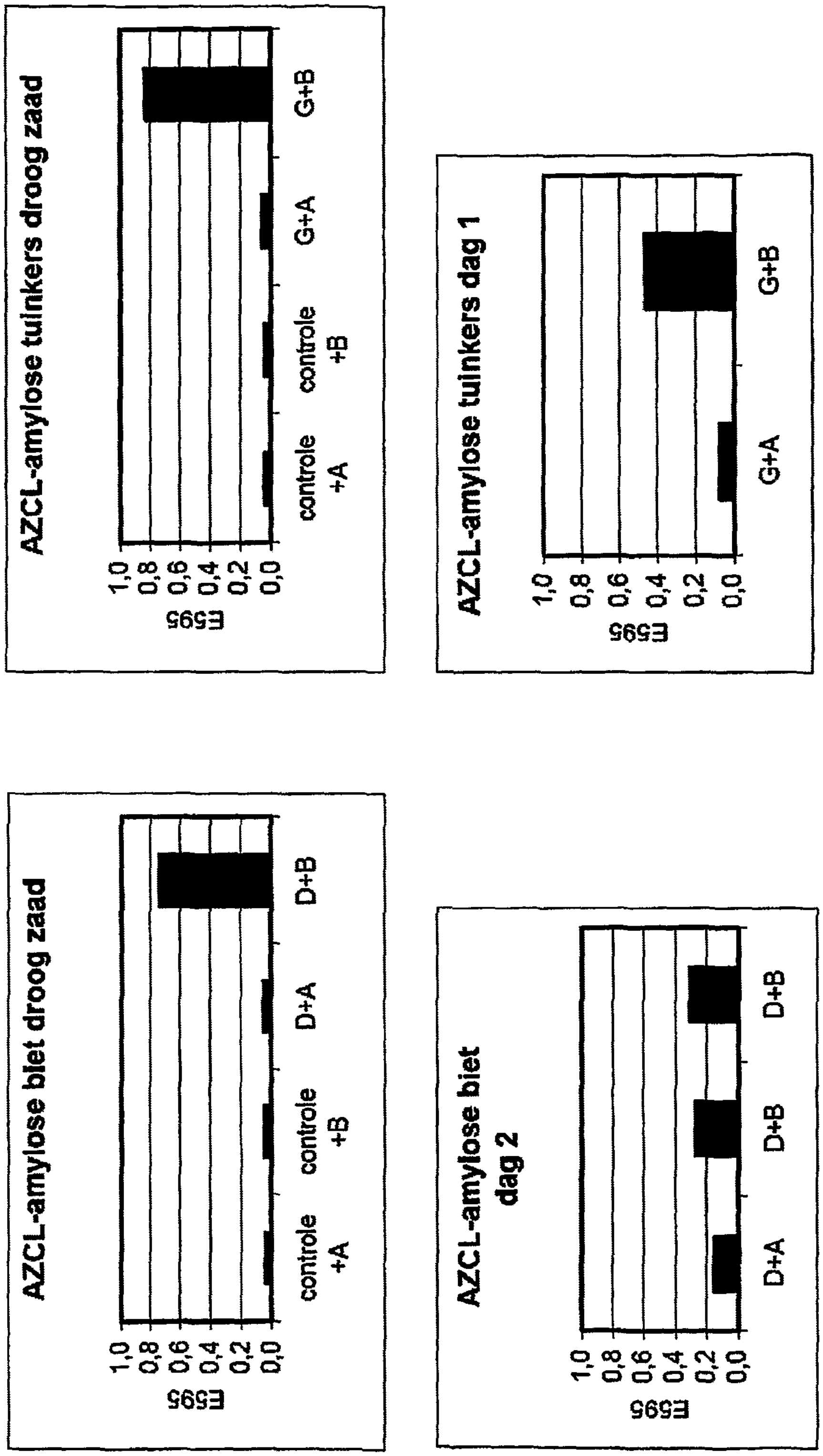

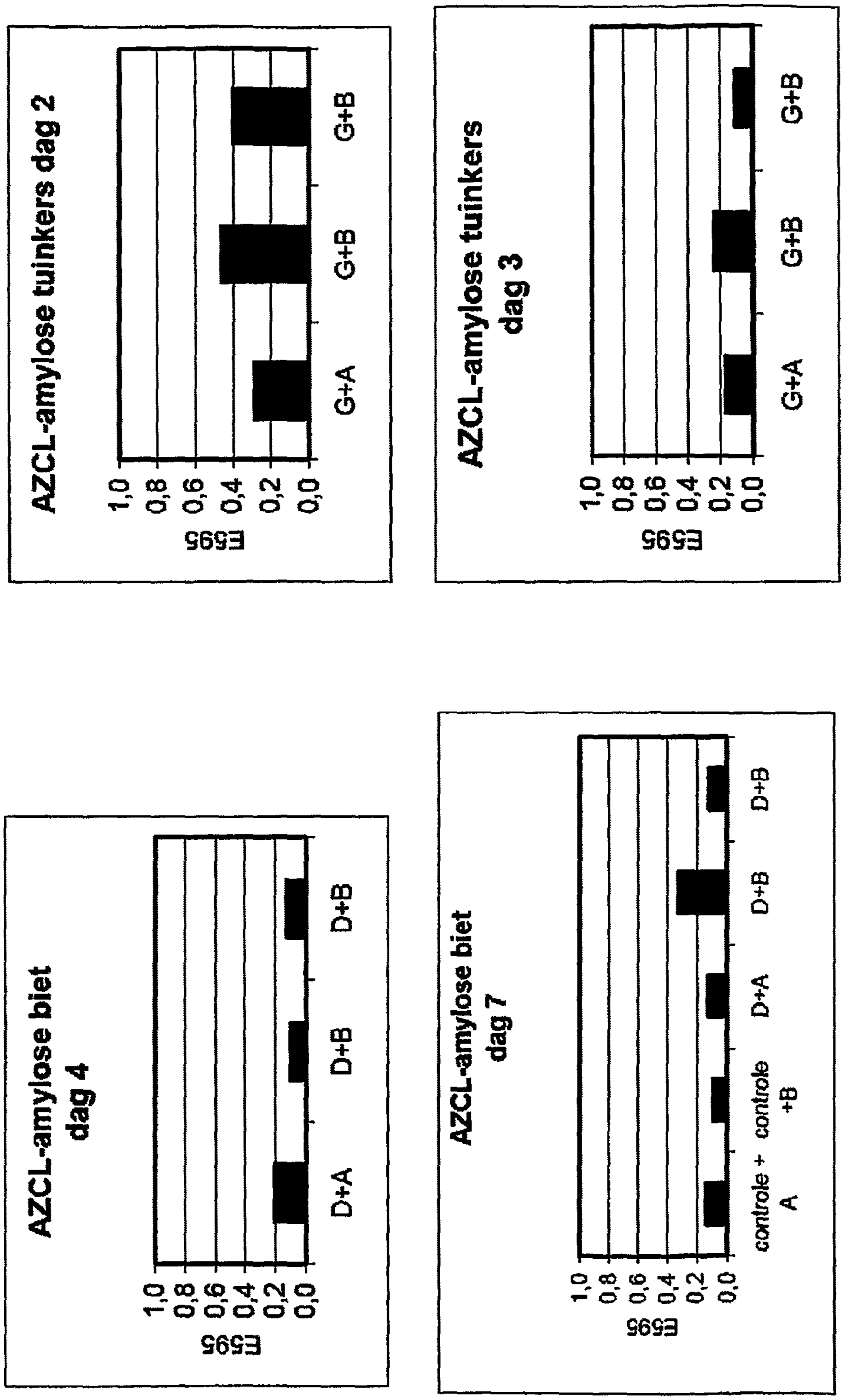
Fig. 13, contd.

METHOD FOR MARKING MATERIALS

This application is a 371 of PCT/NL2008/050453 filed on Jul. 4, 2008, which claims the benefit of European Patent Application No. 07112000.0 filed on Jul. 6, 2007, the contents of each of which are incorporated herein by reference.

FIELD OF THE INVENTION

The invention relates to the field of marking materials with microparticles.

DESCRIPTION OF THE BACKGROUND

Marking of materials is an important feature for identifying the origin of the articles. Traditionally, such marking is accomplished through the packaging of the materials, on which packaging information can be supplied on the producer, content and other features of the packaged materials. However, once the articles are unpacked, said information is lost. This is especially cumbersome if the user of the articles later has a need to identify the origin of the material. Such a need can occur when the articles are malfunctioning. Another use of marking is to prove fraud or forgery. Examples of articles for which marking would be advantageous are clothing, shoes, cigarettes, watches, bank notes, paints, explosives, pharmaceutical products, food products, cosmetic products, animals and agricultural products such as (pot)plants, cuttings, tissue culture materials and seeds.

In the prior art several systems using microparticles for marking materials have been described. Most of these systems use coloured or otherwise labelled microparticles which can provide a code, either by the manner of deposition of the microparticles on the material (thus offering systems which function like a bar-code) or by the intrinsic properties of the microparticles themselves. Examples of such systems are described in (amongst others) U.S. Pat. No. 3,772,099 (luminescent microparticles from a lanthanide and potassium silicate), U.S. Pat. No. 4,390,452 (microparticles forming coloured layers), WO 2003/052025 (microparticles of YVO4 or LaPO4 doped with euridium or cerium), WO 2002/46528 (fluorescent microparticles for forming patterns), U.S. Pat. No. 6,620,360 (multilayers of microparticles) and U.S. Pat. No. 6,455,157 ("bar-coding" with microparticles). In WO 2005/118650 a system is described in which polymer microparticles are doped with a dye, a rare earth element or with radioactivity for marking materials.

WO-A-90/14441 describes a method for tagging a material by treating the material with a nucleic acid taggant so that the nucleic acid attaches to said material in an amount sufficient for subsequent detection. For detection the taggant may be recovered from the tagged material.

Marking of materials is especially important in agriculture in the case of seeds. Once the seeds have been sown, it is practically impossible for a seed supplier to identify if a seed originates from the supplier's company. In this case, the microparticles of the prior art as discussed above are not or less useful, since they are toxic for the seed or the developing seedling, and/or they are dissolved in the earth in which the seeds are sown, and/or they are easy to copy, and/or are already in use for other purposes, other seed lots, other companies etc and therefore are not discriminative.

Thus there is still need for alternative marking microparticles, especially for the marking of seeds.

SUMMARY OF THE INVENTION

The invention thus comprises a method for marking objects comprising applying to said object a microparticle comprising a cross-linked polymer and a marker component wherein the release of said marker component from said microparticle is triggered by contact of the microparticle with an external stimulus and wherein said polymer is a carbohydrate or a protein, or a combination thereof. Preferably in said method the external stimulus is an enzyme, which is able to degrade the polymer, or alternatively the release of the marker component from said microparticle is induced by change of electrostatic interaction, caused by e.g. a change in the pH or a change in the salt concentration.

Further preferred is a microparticle, wherein the polymer of said microparticle is chosen form the group consisting of starch or a derivative of starch, cellulose or a derivative of cellulose, pectin or a derivative of pectin, and gelatine or a derivative of gelatine.

Further preferred is a microparticle, wherein the cross linker is chosen from the group consisting of divinyl sulphone, epichlorohydrin, a di-epoxide such as glycerol diglycidyl ether or butanedioldiglycidyl ether, sodium trimetaphosphate and adipic acid, or derivatives thereof.

Also preferred is a microparticle, wherein the polymer is cross-linked by means of a cross-linking enzyme chosen from the group consisting of peroxidases, laccases, polyphenol oxidases, transglutaminases, protein disulfide isomerases, sulfhydryl oxidases, lysyl oxidases and lipoxygenases.

In said microparticle the marking component is preferably a dye or an enzyme, more preferably laccase. Said marking system is preferably applied to objects chosen from clothing, shoes, cigarettes, watches, bank notes, paints, explosives, pharmaceutical products, food products, cosmetic products, animals and agricultural products such as (pot)plants, cuttings, tissue culture materials and seeds, more preferably seeds.

Also part of the invention is a method for the identification of an object comprising the steps of:

marking the object according to the method of the invention;

identifying said object by applying an appropriate external stimulus to release the marker component from sais micropartile; and assaying for the marker component.

Further, the invention comprises the use of a microparticle comprising a charged cross-linked polymer and a marker component wherein the release of said marker component from said microparticle is triggered by contact of the microparticle with an external stimulus and wherein said polymer is a carbohydrate or a protein, for marking objects.

Further, the invention is directed to a kit for marking an object or for the identification of an object, comprising microparticles as defined herein; and an enzyme for degrading the polymer.

Further, the invention is directed to a kit for marking an object or for the identification of an object, comprising microparticles as defined herein; and a salt for releasing the marker component.

LEGENDS TO THE FIGURES

Figure 1A:
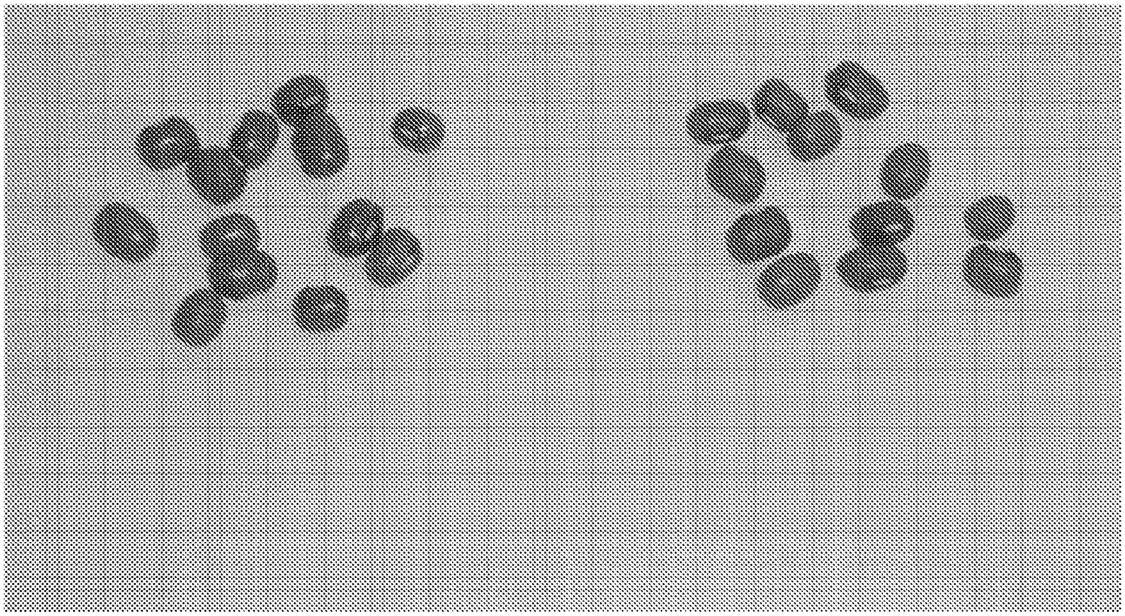
Figure 1A:
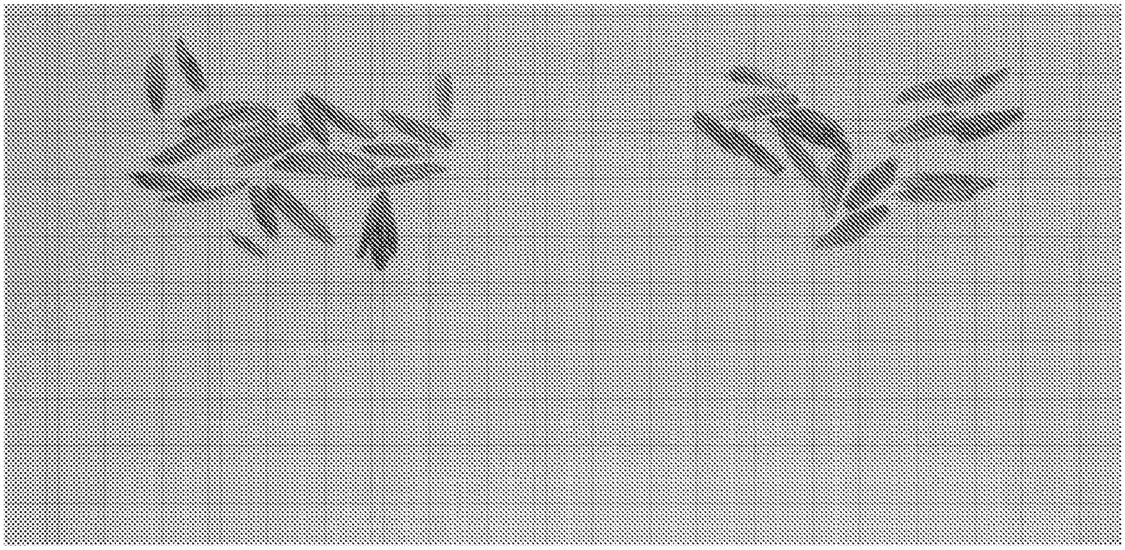
Figure 1B:
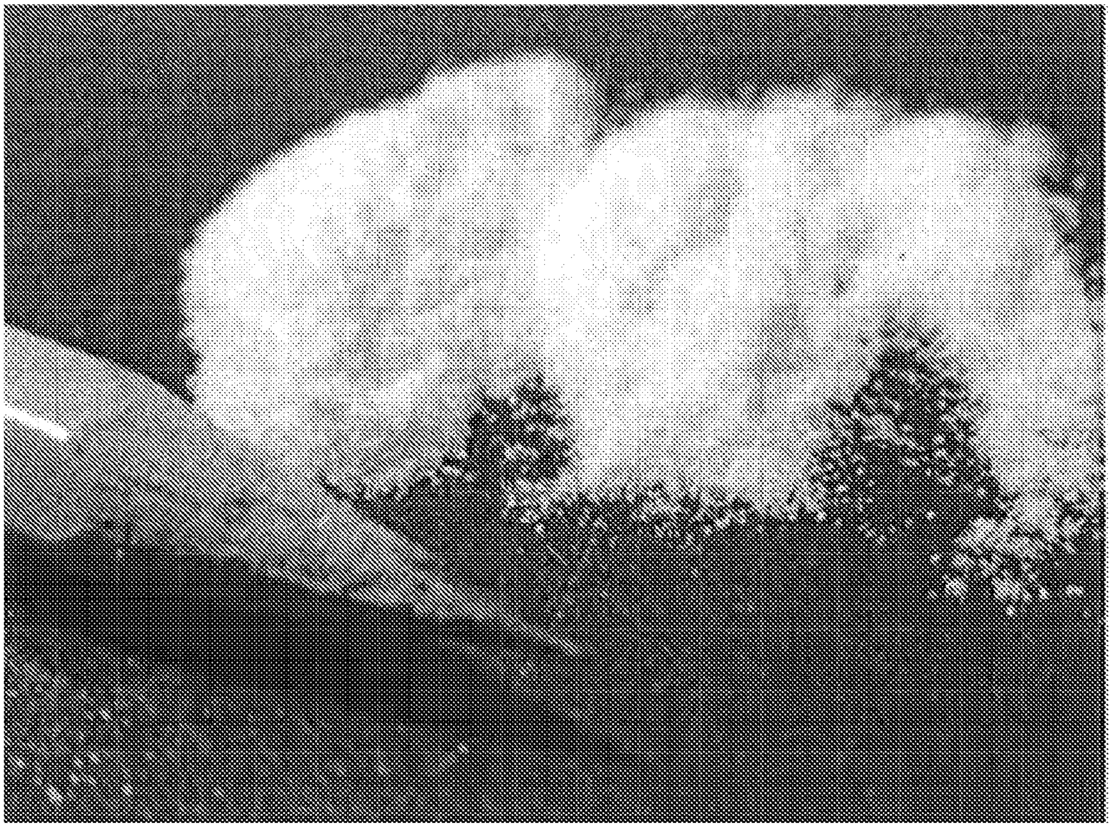

FIG. 1. A. Mung beans and grass seeds, both coated with Phenolphthalein-containing WDV86-88 particles and uncoated. B. example of dried BioSwitch particle, i.e. finely ground.

Figure 2:
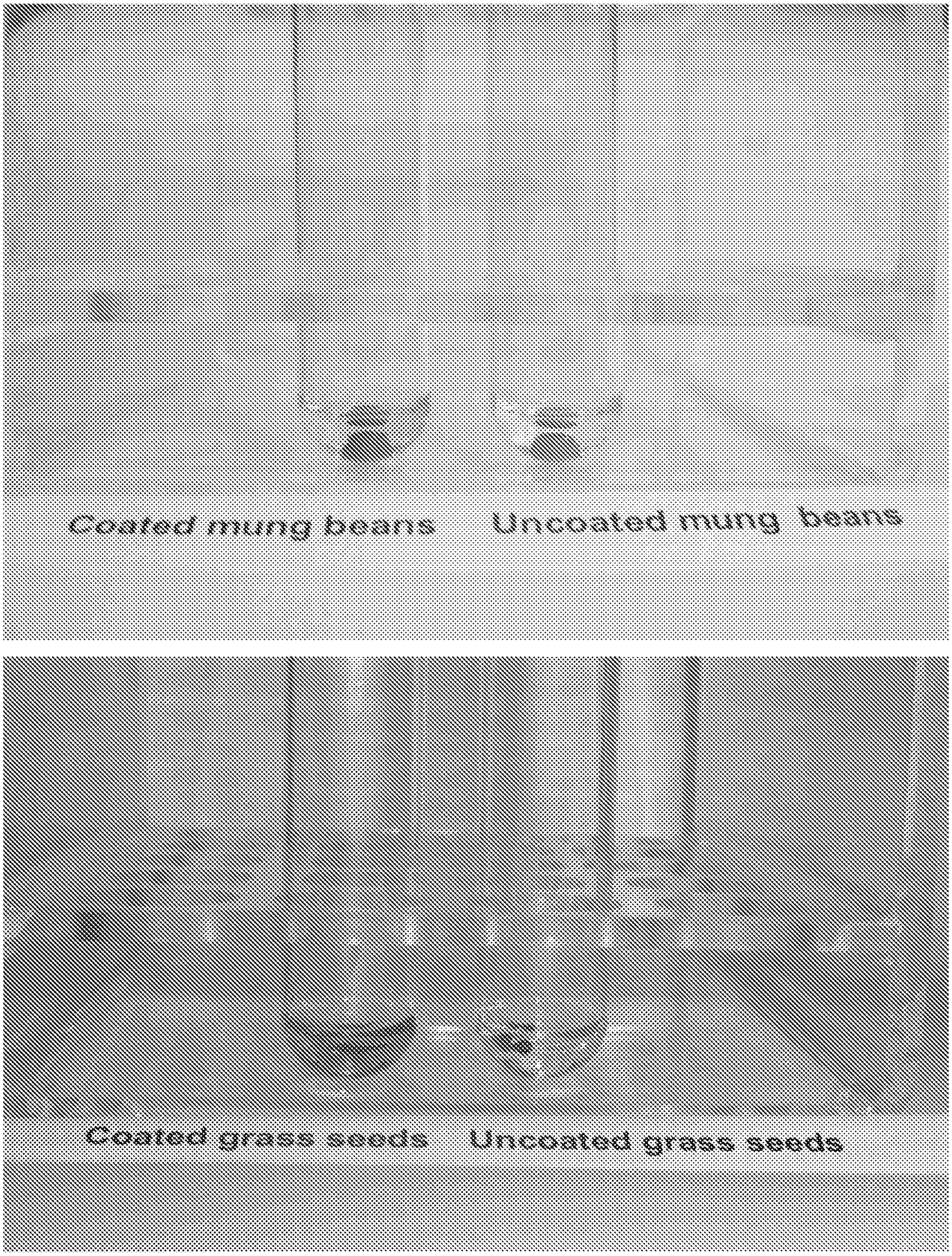

FIG. 2. Mung beans and grass seeds, both coated with Phenolphthalein-containing WDV86-88 particles and uncoated in test solution: 50 mM sodium carbonate buffer pH 10.

Figure 3:
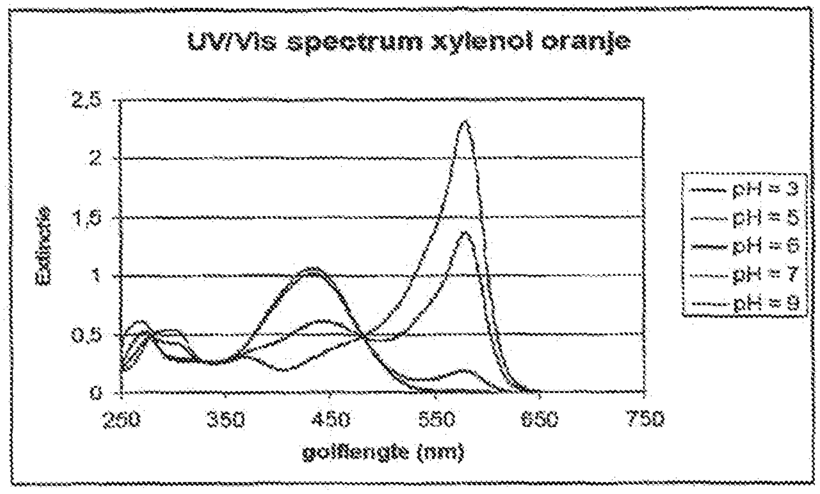

FIG. 3. UV/Vis spectrum of Xylenol orange at different pH values.

Figure 4:
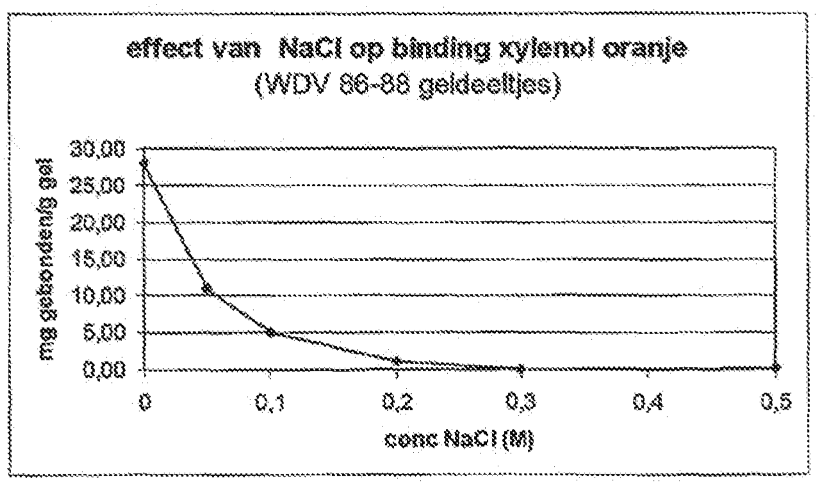

FIG. 4. Salt dependence of the interaction between Xylenol orange and the cationic WDV86-88 matrix.

Figure 5:
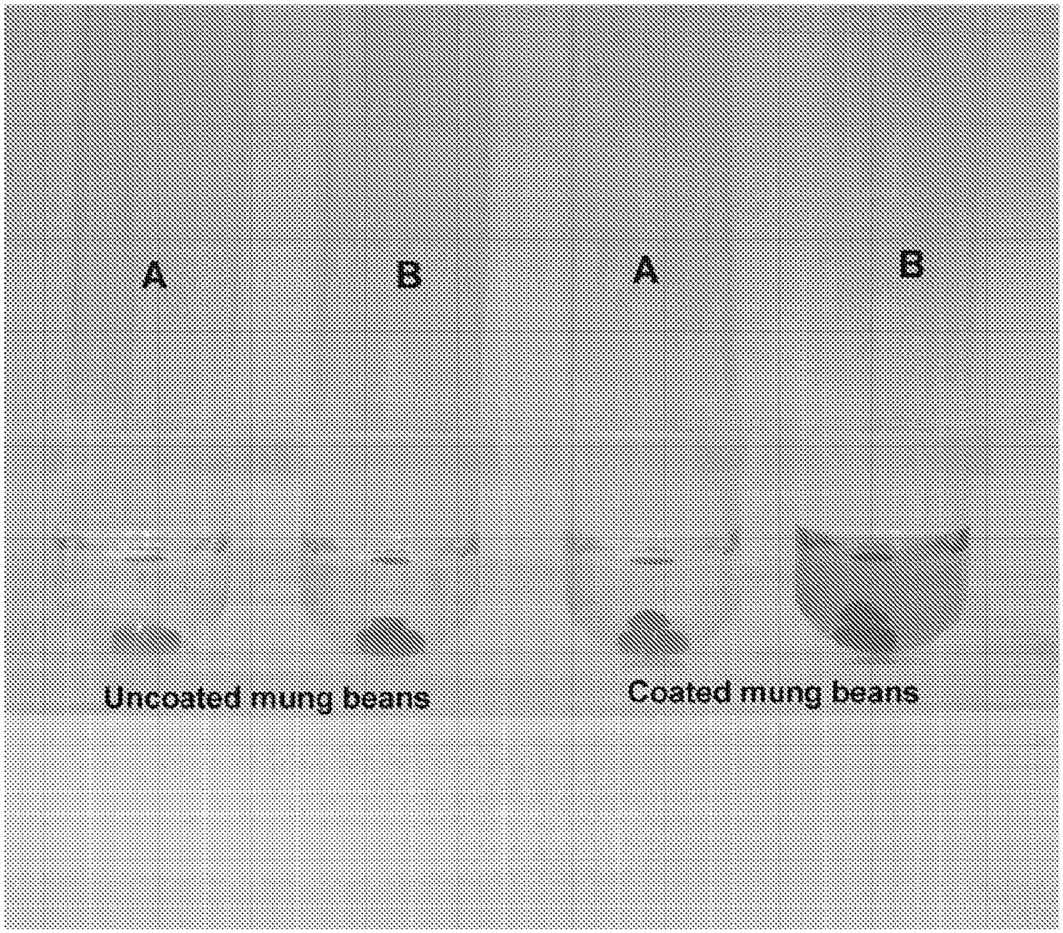

FIG. 5. Xylenol orange containing WDV124 gel particles coated mung beans as compared to uncoated mung beans. Test solution A: 5 mM TRIS/HCl pH 8.0; Solution B: 50× diluted Thermamyl Amylase in 5 mM TRIS/HCl pH 8.0.

Figure 6:
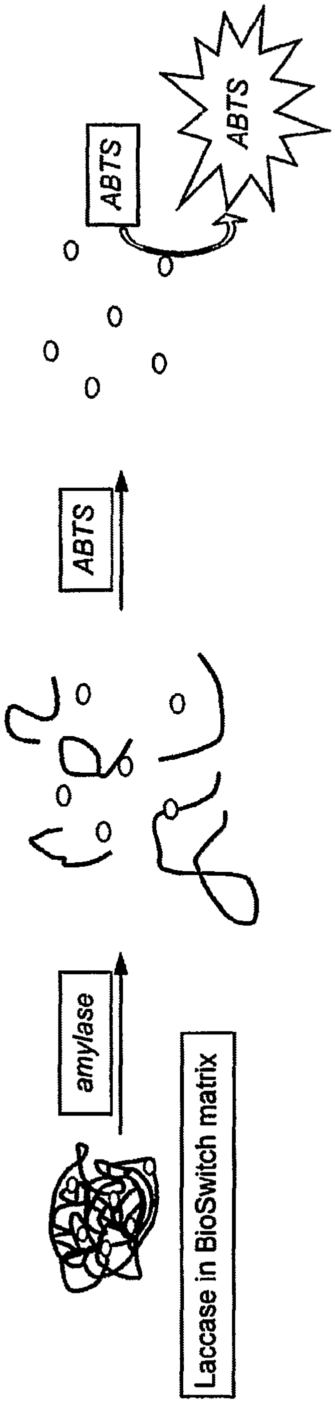

FIG. 6. A two-step Optical marker concept.

Figure 7:
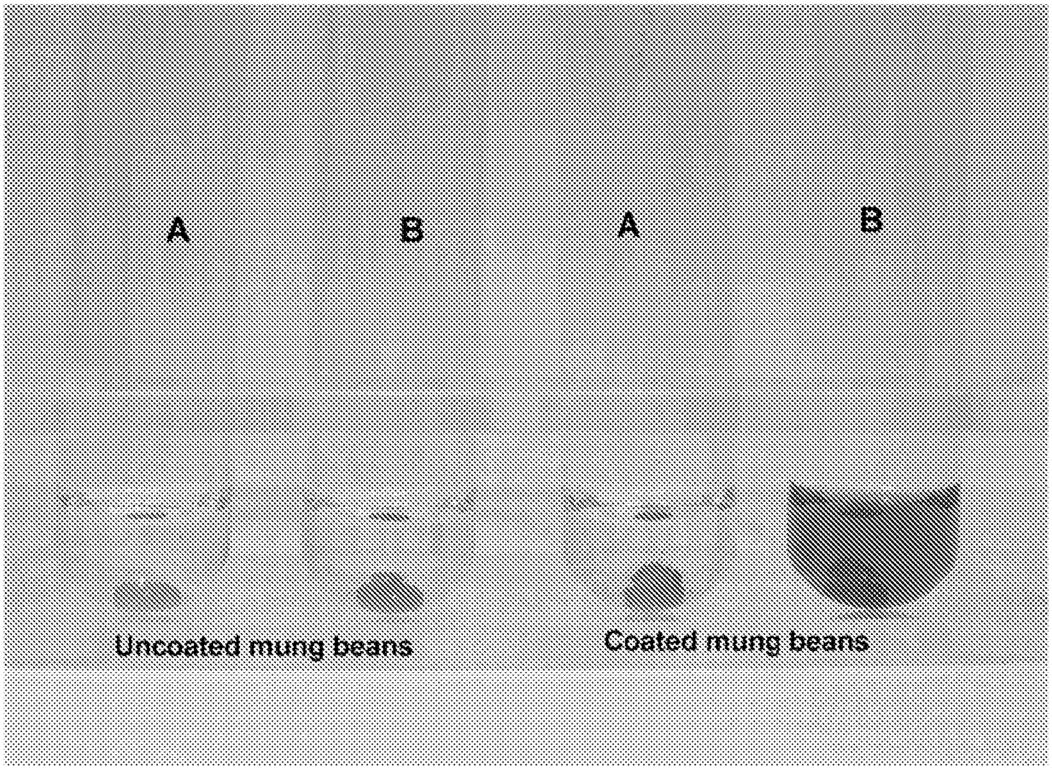
Figure 7:
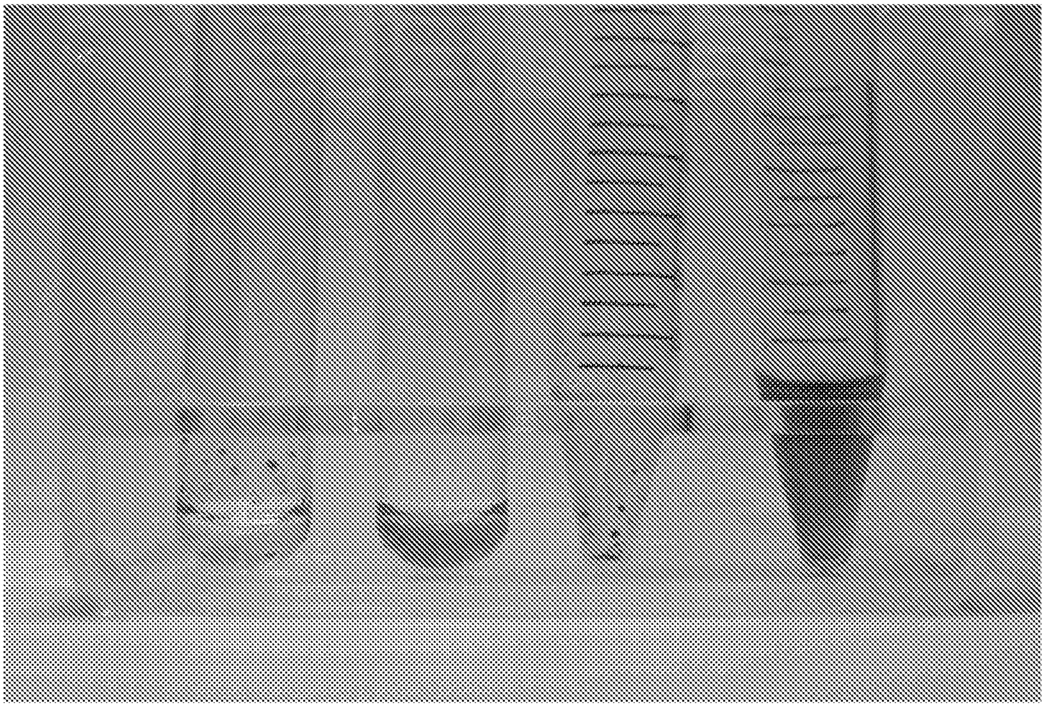

FIG. 7. Upper panel: Laccase containing WDV124 gel particles (lyophilized) coated Mung beans as compared to uncoated mung beans. Test solution A: 5 mM TRIS/HCl pH 8.0; Solution B: 50× diluted Thermamyl Amylase in 5 mM TRIS/HCl pH 8.0. ABTS was added after 10 min incubation at ambient temperature; picture was taken 2 min thereafter. Lower panel: the two tubes on the right-hand side contain free BioSwitch particles (i.e. not coated on seeds). Amylase to decompose the starch-based BioSwitch matrix was only allowed to react for 10 min in tube B. In both cases ABTS was added thereafter.

Figure 8:
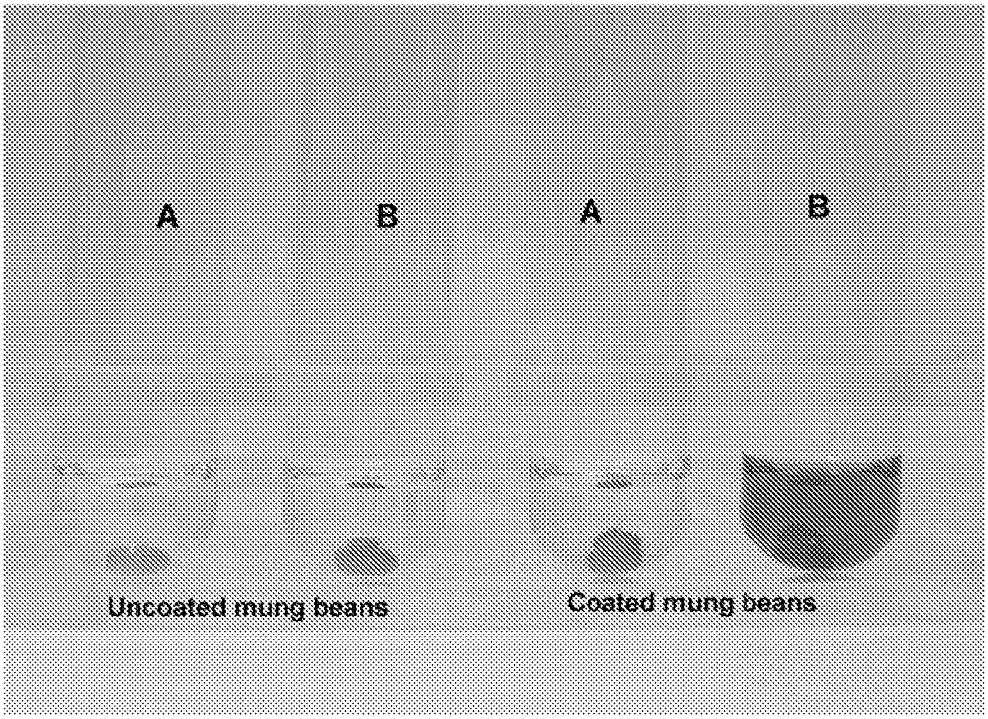
Figure 8:
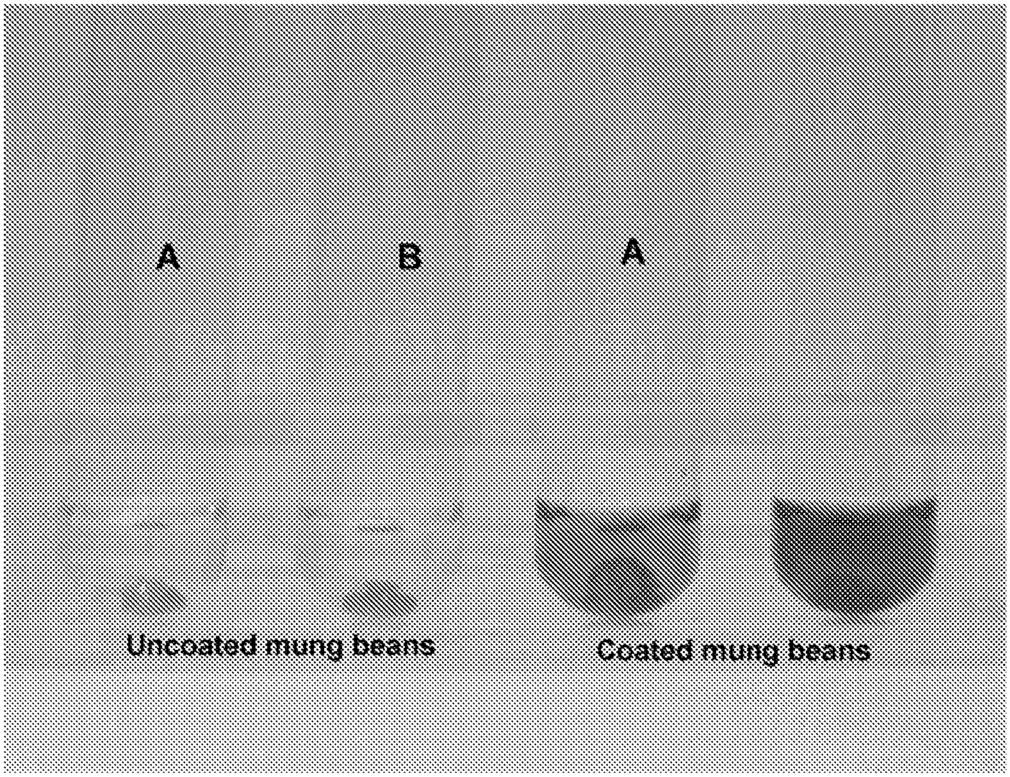

FIG. 8. Laccase containing WDV124 gel particles (lyophilized) coated mung beans as compared to uncoated mung beans. Test solution A: 5 mM TRIS/HCl pH 8.0; Solution B: 50× diluted Thermamyl Amylase in 5 mM TRIS/HCl pH 8.0. ABTS was added after 10 min incubation at ambient temperature; pictures were taken 8 and 210 min thereafter, for the upper and lower panel, respectively.

Figure 9:
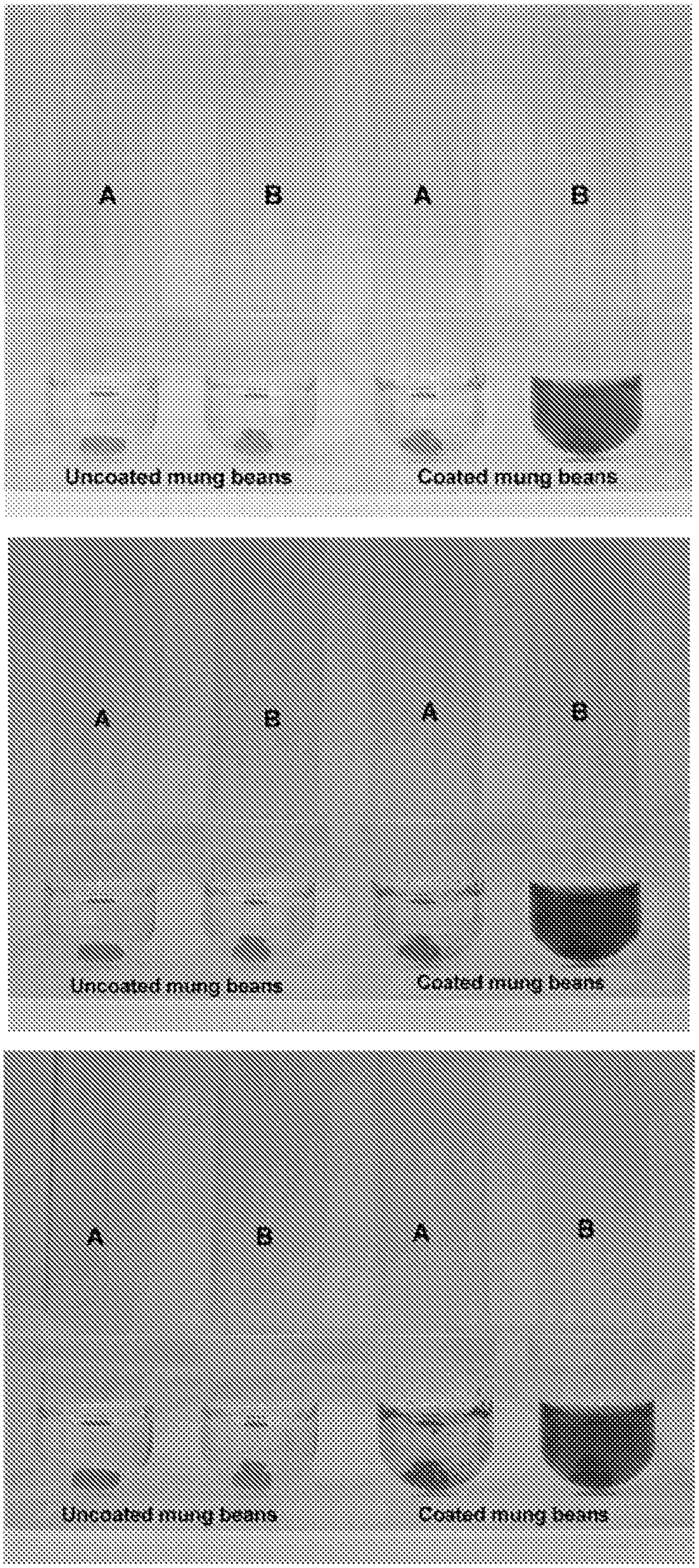

FIG. 9. Laccase containing WDV124 gel particles (air-dried) coated mung beans as compared to uncoated mung beans. Test solution A: 5 mM TRIS/HCl pH 8.0; Solution B: 50× diluted Thermamyl Amylase in 5 mM TRIS/HCl pH 8.0. ABTS was added after 10 min incubation at ambient temperature; pictures were taken 30 s, 2 and 15 min thereafter, for the upper and lower panel, respectively.

Figure 10:
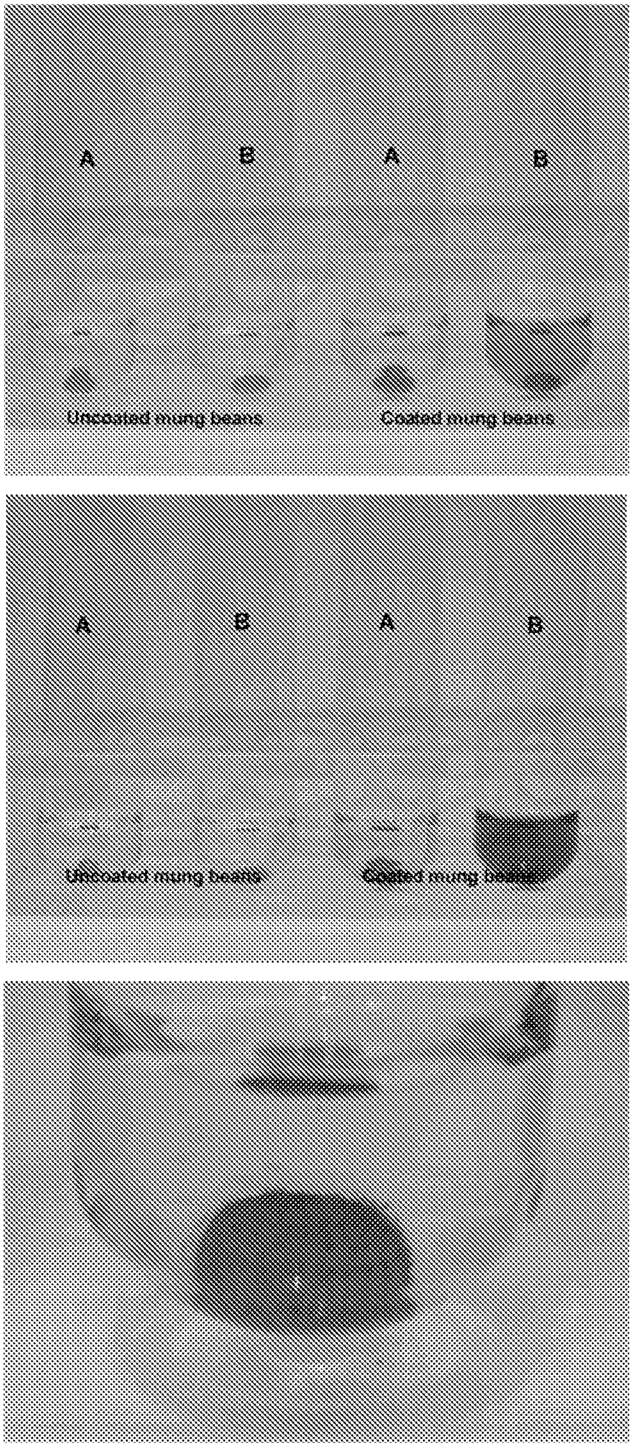

FIG. 10. Laccase (batch 2) containing WDV124XF gel particles (lyophilized) coated mung beans as compared to uncoated mung beans. Test solution A: 5 mM TRIS/HCl pH 8.0; Solution B: 50× diluted Thermamyl Amylase in 5 mM TRIS/HCl pH 8.0. ABTS was added after 10 min incubation at ambient temperature; pictures were taken 1 and 5 min thereafter, for the upper and middle panel, respectively. The lower panel shows a close-up a coated mung beans in test solution A, incubated with ABTS.

FIG. 11. Laccase activity as measured on beetroot seeds (left-hand panel) and garden cress seeds (right-hand panel), i.e. on seeds as such, and after 2, 4 and 7 days (beet); or 1, 2 and 3 days (cress).

FIG. 12. Presence of Xylenol orange as measured on beetroot seeds (left-hand panel) and garden cress seeds (right-hand panel), i.e. on seeds as such, and after 2, 4 and 7 days (beet); or 1, 2 and 3 days (cress).

FIG. 13. AZCL-Amylose as measured on beetroot seeds (left-hand panel) and garden cress seeds (right-hand panel), i.e. on seeds as such, and after 2, 4 and 7 days (beet); or 1, 2 and 3 days (cress).

DETAILED DESCRIPTION

The microparticles according to the present invention comprise a cross-linked carbohydrate and/or protein, made of oligomeric and polymeric carbohydrates and/or proteins which can be used as a substrate for any external stimulus, such as an enzyme. Carbohydrates which can thus be used are carbohydrates such as, for instance, glucose, fructose, sucrose, maltose, arabinose, mannose, galactose, lactose and oligomers and polymers of these sugars, cellulose, dextrins such as maltodextrin, agarose, amylose, amylopectin and gums, e.g. guar. Proteins which can be used include albumin, ovalbumin, casein, myosin, actin, globulin, hemin, hemoglobin, myoglobin and small peptides. Preferably, oligomeric carbohydrates from DP2 on or polymeric carbohydrates from DP10 on are used. More specifically, polymeric carbohydrates of >DP50 and even more specifically of >DP75 are used. These can be naturally occurring polymers such as starch (amylose, amylopectin), cellulose and gums or derivates hereof which can be formed by phosphorylation or oxidation. Other polymers can also be used (e.g. caprolactone), which can be added for a better compatibility with e.g. the material to be marked. In the case of proteins, proteins obtained from hydrolysates of vegetable or animal material can also be used. Also suitable mixtures of carbohydrates (e.g. copolymers) or mixtures of proteins can be used.

It is possible that synthetic polymers are used, such as for example: polyvinyl, polyethylene, polypropylene, and similar compounds.

The advantages of cross linked polymers lies in the intrinsic stability of the vehicles formed through the introduction of cross links in the matrix. Specifically, the crosslinks are ether- and/or ester-links, where for the ester-links phosphate-esters are preferable. A further important advantage is that cross-linking provides a three-dimensional lattice of the cross-linked polymer, in which a component, which is to serve as marker, can be "filled in". Moreover, the choice of components, i.e. the choice of polymer(s) and cross-linker(s) influences the three-dimensional structure of the vehicle and thus would allow for the manufacture of specific vehicles suited for molecules of a certain size and/or certain charge.

The polymer matrix from which the microparticle is built may be constructed from readily available and water soluble polymers such as polysaccharides and (hydrolysed) proteins and in doing so a flexible matrix may be formed and positive and/or negative charge through e.g. carboxylic acids and/or cationic groups will generate a custom made vehicle for the marking component. This cannot be accomplished using polysaccharides such as chitin and/or chitosan. Also the above mentioned polymers are much cheaper than the hitherto used chitin and chitosan. The possession of a charge is a most important feature of a polymer for the present invention. It will greatly facilitate the formation of a complex between the marking component (which is often a charged molecule) and the polymer lattice. Preferably, the polymers are charged. Such a charge can be provided by the polymer itself, but—if the polymer does not have a positive or negative charge—the charge can be introduced as a result of modification of the polymer or by the cross-linker used for cross-linking the polymer.

The formation of the matrix is accomplished through covalent cross linking of the polymers. Typical cross linkers, that can be used, are chemical cross-linking agents such as divinyl sulphone, epichlorohydrin, a di-epoxide such as glycerol diglycidyl ether or butanedioldiglycidyl ether, sodium trimetaphosphate and adipic acid or derivatives thereof, or glutaraldehyde and the like. Cross-linking can also be established by enzymatic action, e.g. by using enzymes from the group consisting of laccases (which e.g. induce cross-linking of pectins), peroxidases, polyphenol oxidases, transglutaminases, protein disulfide isomerases, sulfhydryl oxidases, lysyl oxidases and lipoxygenases. Methods how to use these cross-linkers or cross-linking enzymes are well known in the art and/or have been abundantly described in the experimental part.

Modification of the polymers can be accomplished by oxidation, substitution with cationic functional groups or carboxymethyl groups and/or esterifying with e.g. acetyl groups. Although in the latter case no charge is added, it is used to make the polymer more hydrophobic to allow complexing of the polymer with marking components that have little or no charge.

Generally the polymers will be modified before cross-linking and gelation. Only if cross-linking by ether-forming has been done it is possible to modify the polymer after cross-linking and gelation. The person skilled in the art will know how to modify the polymers specified in the invention to provide them with the mentioned groups.

The charge of the cross-linked polymer can be negative or positive depending on the type of polymer, the type of modification and the type of cross-linking.

Advantageously, the polymers are of considerable size, i.e. 30 kD or more. This allows for the ready formation of a gel upon cross-linking and it allows for the formation of a lattice which is capable of taking up the marking component.

The microparticles of the inventions are made by cross-linking readily available carbohydrate polymers and/or proteins. Preferably, the cross-linked polymers form a gel, as shown in the Examples, which ensures a long stability of the microparticles and an easy further employment of the microparticles for marking articles and materials.

In general the method of making the microparticles is as follows:

a) provide a polymer;
b) provide a cross-linker or cross-linking enzyme and activating the cross-linker by addition of a base or an acid;
c) add the cross-linker to the polymer; it is to be understood that activation of the cross-linker may occur before mixing the polymer and the cross-linker, or when both already are mixed. This depends on the type of cross-linker and the type of polymer that is used;
d) allow for cross-linking to occur;
e) allow for gelation of the cross-linked polymer;
f) wash the gel to remove all solvents and reagents that have not reacted;
g) form microparticles from the gel by breaking the gel and optionally further milling;
h) dry the microparticles; and
i) load the vehicles with the marking component.

This method allows for the formation of suitable microparticles according to the invention. As polymer base also mixtures of proteins and carbohydrates can be used in this process.

In this way microparticles are formed that are stable and can be used in the various applications according to the invention. The Examples below show that the microparticles will not gelate again when solved, even not when heated or boiled, and they do not spontaneous fall apart which would cause untidy release of any marking component.

The size of the microparticles depends on the breaking and grinding process. Breaking is preferably done by pressing the gel through a sieve of a desired mesh size. If necessary, finer particles can be formed by additional grinding the sieved particles. The size of the vehicles preferably can range from 0.5 μm to 100 μm and the optimal size will depend on the specific application for which they are used. It is generally thought that small microparticles are preferable for applications where marking should be invisible (such as on bank notes), where larger microparticles can be used where visibility or size is not limiting, such as in seed coating.

It is thought that loading of the marking component is possible because complexes are formed due to electrostatic interactions between the charged groups of the cross-linked polymer and the charged groups on the compound of interest. In the case that neutral components and/or polymers are used complex formation will probably be caused by hydrostatic interactions between hydrophobic groups.

The marking component can be of any size and weight, as long as the microparticles can accommodate stable complexing with said compound, but it will preferably have a weight of less than 50 kD, more preferably less than 30 kD and most preferably less than 10 kD. In the case that enzymes, or other proteins, are used as marking component the size and weight can easily be more than 50 kD. The marking component which is available in the microparticle will not be released from said microparticle unless an external stimulus changes the property of the vehicle. This has the advantage that the marking component is not spilled to the environment or onto the article, which is marked with the microparticles. The stimulus can be of any origin, as long as it is able to open up the vehicle or reduce the complexation of the marking ingredient with the microparticle lattice so that the marking component will be released from the microparticle. Basically there are two kinds of stimuli that can be employed, namely through electrostatic interaction between the microparticle and the marking ingredient or through hydrolysis of the polymers.

Electrostatic interaction effects can be accomplished through changes in pH, salt concentration or other general mechanisms. Generally this will result in the exchange of the marking component with the free ions of the solution. Hydrolysis of the polymer chains can be accomplished via the action of acids or bases or, preferably, enzymes.

In a preferable embodiment, the invention encompasses microparticles in which the external stimulus which is able to trigger the vehicle to decompose is an enzyme which is able to degrade the polymer. A large number of enzymes which can convert the above mentioned polymers whereupon the embedded active component is released, are known, such as amylase, hemicellulase, xylanase, glucanase, pullulanase, arabinodase, cellulase, pectinase, mannanase or peptidase or protease. The advantage of the fact that the marking components are complexed with the microparticles of the invention is not only a release only by an external stimulus but also the side-effect that the marking compound is preserved by the microparticle and will not be degraded by environmental influences (except, of course, if the external stimulus is present). Furthermore, most of the polymers that can be used for the production of the microparticles are not toxic, and even are foodgrade ingredients.

It is also possible, according to the present invention, to provide two or more marking components. This can be achieved by mixing microparticles loaded with different components or by providing a loading solution with two or more marking components solved therein for loading the microparticles (i.e. performing step (i) of the method described above).

The advantage of the present invention is that the marking substance will only be released from the microparticle when the external stimulus is applied. Thus, the microparticles on the marked materials will be practically inert until the loaded marking substance will be released.

In one embodiment of the invention a coating comprising microparticles with a marking substance can very well be used to be applied onto materials, even on surfaces which often come into contact with foods or onto vulnerable systems, such as (the cut stems of) cut flowers, plant roots, cuttings used as propagating material, plant tissue culture materials, nutrient supporting and plant supporting media of rock wool or other material, etc. Coating this type of materials using a coating according to the invention does not hinder the functions (e.g. water or nutrient intake) of the materials, but still provides the desired marking.

Coatings according to the invention can preferably be used to coat seeds. Seeds are often provided with coatings to provide fungicides, insecticides, pesticides, nutrients and other compounds for the sprouting seedlings, the young plants and/or developing crop. The microparticles loaded with the marker components according to the present invention can be easily applied to the seeds, either as part of and in the process of normal coating, or as a separate coating. Alternatively, the microparticles could be included in seed pellets, or in the coatings applied to pelleted seeds. A pellet is a generic term used for a small particle or grain, typically one created by compressing an original material. In seed treatment, pelletizing means encapsulating the seed into a sphere of clay filler, which greatly improves the handling characteristics of the seed as well as providing a vehicle for seed treatment chemicals. Pelletization mixtures typically comprise various types of organic or inorganic fibers, clays and inert inorganic materials, and contain also particles with internal open porosity. Other frequently used types of pelletization mixtures are various combinations of clays with inert raw materials without the addition of fibers. The microparticles of the present invention can be included into the pelletizing mixture top be applied onto the coats. Alternatively, since seed pellets are often coated with a polymer film coating to apply beneficial compounds to the seed, the microparticles of the present invention can also be applied to the coating.

Further, the coating of the seeds does not need to envelop the seeds totally, it would be sufficient if several microparticles would adhere to the seed, such that each seed is marked and would be prone to being identified by assaying for the marker. It is a prerequisite that the microparticles shall not be detrimental to the seed, nor shall be detrimental to the developing seedling. Also residual microparticles should not be harmful for the environment or when they would end up in edible substances (such as roots, tubers or other parts of the plant). These goals can easily be reached according to the present invention.

The marker substances which may be used in the microparticles can be any compound that can be specifically identified. For practical use preferred marker substances are specifically identified with easy, fast and cheap methods. Such marker substances can be optical markers, such as natural dyes, chromophores or fluorescent or phosphorescent compounds, compounds with specific NIR absorption or fluorescence spectrum, compounds with a specific Raman spectrum, enzymatic markers, such as laccase, or any other enzymes, that are incapable of degrading the polymer of the microparticle, biopolymers such a nucleotide sequences, chemical compounds such as pH indicators, or any combination of the above. Marker substances may also be substances that can be identified by a specific chemical reaction or physical interaction with other compounds that are added in an identification assay. Substances that can be identified specifically with sensors or sensor systems may also be used as marker substances.

For instance enzymes, such as laccase can be used as marker substance in the microparticles. After the appropriate stimulus (e.g. amylase), the microparticle is degraded, whereby the enzyme is released. Then, the marker enzyme is present, which can be detected by adding a second component. In case of laccase, the second component would be ABTS, which is a model substrate for this enzyme. The ABTS will be oxidized by the laccase and change colour from colourless to green. In the case of seeds marking, a seed marked with the microparticles of the invention will be added to a solution containing the stimulus for degradation of the microparticle, e.g. an enzyme. Then, the reactant which is able to react with the marker is added to the solution and the (colour) reaction is observed. The person skilled in the art will be able to use specific reactions fitting the above scheme in the current invention. As indicated above, one example is the use of laccase as marker and ABTS as reactant, other examples would be combinations of antigen and labeled antibodies; nucleic acids, of which the reactant is labeled, which are able to hybridise; etc. It is even possible to have three-step reaction schemes, where the marker is reacted with a reactant, which would yield a product and where the product is detectable via a second reactant.

Preparation and use of the vehicles of the invention will be shown in the Examples. A person skilled in the art will understand that the invention is not limited to the specific embodiments and uses mentioned, but that the invention can be manifested in various other embodiments which will be readily available to said person.

EXAMPLES

Example 1

Preparation of Microparticles (Bioswitch Particles)

To a solution of 2.4 grams NaOH in 480 ml water, 120 grams of potato starch was added and gelatinized by incubation at 65° C. When the starch was completely dissolved, 73 ml of glycidyl trimethylammoniumchloride (70% in water) was added to introduce cationic functional groups. The reaction mixture was stirred at 60° C. for 120 minutes. After cooling to room temperature 1 g NaOH (dissolved in 2 ml water) was added to 100 ml of the obtained reaction mixture. Then 2 ml glyceroldiglycidylether was added for crosslinking the cationized starch, followed by stirring for 15 min. This solution was stored at 3° C. for 3 days. After cooling to room temperature, the resulting gel was pressed through a sieve with meshes of approximately 1 $mm^2$, after which water was added, which was readily absorbed by the gel. The gel was then precipitated with ethanol, washed subsequently twice with ethanol and once with acetone, and air-dried in a gel drier.

Two types of gels were used for experiments concerning optical markers:

| Code | % degree of substitution (cationisation) | % crosslinking | sensitive to amylase degradation |
|---|---|---|---|
| WDV86-88 | 52 | 6 | low |
| WDV124 | 30 | 4.4 | high |

Example 2

Incorporation of Phenolphthalein or Xylenol Orange into Gel WDV86-88

Approximately 200 mg of phenolphthalein was dissolved in 20 ml of ethanol. 2.4 g of gel particles (WDV86-88) was added and allowed to swell under vigorous shaking. The solution was readily absorbed by the gel (within 30 sec). Thereafter, the reaction mixture was lyophilized, resulting in approximately 2.2 grams of dried white gel particles.

As an illustration, mung beans and grass seeds coated with Phenolphthalein-containing WDV86-88 particles are depicted (FIG. 1). Compared to uncoated particles, the CMC coating with BioSwitch particles is hardly visible.

Clear differences between coated and uncoated seeds, become apparent when a suited test solution is applied (FIG. 2). The test solution lead to a release of Phenolphthalein from the BioSwitch particles. In addition to release, this test solution resulted in an increase of the pH (above pH 9, Phenolphthalein changes from colourless to purple).

Although this concept works, disadvantages are that the active compound was released without an external trigger. In addition, it is too easy to copy (a simple coating with Phenolphthalein will also do the trick).

50 mg of gel particles (WDV86-88) were allowed to swell under stirring in 10 ml Milli Q water for 1 hour. Then, 1.5 mg of the dye Xylenol orange dissolved in 0.5 ml Milli Q was added. All dye was absorbed by the gel within 15 min (ionogenic interaction). Binding of Xylenol orange to the gel, resulted in the dye to change colour from yellow to deep red.

Sodium chloride was added to 0.5 ml of a Xylenol orange-incorporated WDV86-88 gel particles suspension, to reach an end volume of 2 ml, having the following end concentration of NaCl: 0; 0.05; 0.1; 0.2; 0.3; 0.5; and 1 M. After 30 min of stirring, the gel particles were removed from the suspension by centrifugation (5 min 3700 rpm). The Xylenol orange concentration in the resulting clear supernatant was determined by measuring the extinction at 480.2 nm. By using a reference solution, it was determined that 1 extinction unit at 480.2 nm corresponds to 0.0625 mg of Xylenol orange. It was found that no substantial influence of the pH on the extinction of Xylenol orange was observed at this wavelength (isosbestic point).

The UV/Vis spectrum van Xylenol orange was determined in respectively the following buffers (all 50 mM): malic acid pH 3.0; acetate pH 5.0; MES pH 6.0, BisTRIS propane pH 7.0; and, BisTRIS propane pH 9. The spectra were recorded at the various pH values, using Xylenol orange in a final concentration of 0.03 mg/ml.

The UV/Vis spectrum of Xylenol orange at different pH values is depicted in FIG. 3. It is an interesting molecule because of its four negative charges (4 carboxyl groups). Therefore, it was expected to have a fairly good electrostatic interaction with a cationic BioSwitch matrix. In addition, because it can be protonated/deprotonated at four positions, Xylenol orange will have different colours at different pH values. This makes it an interesting compound with respect to optical markers. The structural formula of Xylenol orange is depicted below.

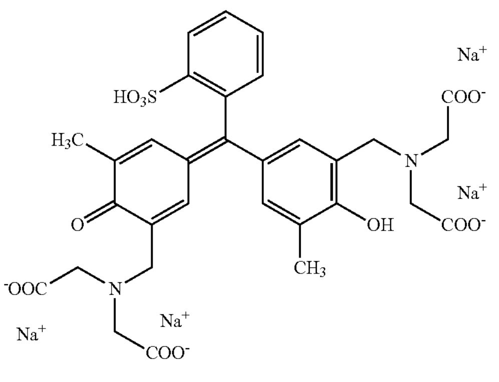

At a wavelength of 480.2 nm, the extinction appeared to be hardly affected by the pH, making this an isosbestic point.

The extinction at this pH can be used for determination of the Xylenol orange concentration in solution.

The effect of salt (NaCl) on the binding of Xylenol orange to WDV 86-88 gel is depicted in FIG. 4. It shows that the 4 negative charges resulted in a sufficient interaction with the cationic matrix, especially at lower ionic strength.

For demo experiments, Xylenol orange loaded gel particles were applied to seeds. It appeared, however, that when 5% CMC was used to coat the BioSwitch particles to mung beans, a substantial amount of Xylenol orange was already released. No real difference was observed in the test tubes with or without Amylase (which was used to decompose the gel particles, in order to release the dye). The conductivity of the used CMC was measured and found to be 7.2 mS/cm; corresponding to the ionic strength 0.1 M NaCl. To decrease the ionic strength of the coating material, a 2% solution of gelatinized starch was used for further experiments.

Example 3

Incorporation of Xylenol Orange into WDV124 Gel Particles 2.5 g of WDV124 gel particles were allowed to swell under stirring in 380 ml Milli Q, for 1 hour. Then, 20 ml of 50 mM MES/NaOH pH 6 buffer was added, followed by the addition of 150 mg of Xylenol orange in 50 ml Milli Q. Nearly all dye was absorbed by the gel within 30 min. Binding of Xylenol orange to the gel, resulted in the dye to change colour from yellow to deep red. Thereafter, the gel was lyophilized, resulting in 2 grams of deep-red coloured powder.

Example 4

Coating of Seeds or Beans with Marker Loaded WDV86-88 Gel Particles

Seeds (from grass, beetroot or mung beans) were moisturized with a 5% solution of carboxymethyl cellulose (CMC). Dry gel particles WVD86-88 were added, thereby aiming at a uniform distribution of the marker loaded gel particles over the seeds. This was achieved by shaking the seeds during addition of a household sieve. Subsequently, the coated seeds were dried by means of a blow-drier.

Coating of mung beans with phenolphthalein-containing WDV124 gel particles went as follows:

Mung beans were moisturized with a 2% solution of gelatinized starch. Dry gel particles (WDV124) were added, thereby aiming at a uniform distribution of the gel particles over the seeds (approx. 0.25 mg of particles per bean). This was achieved by shaking the seeds during addition of a household sieve. Subsequently, the coated seeds were dried by means of a blow-drier.

Coating of seeds with CMC gave no good result in this case: the ionic strength of CMC was above the threshold value, thereby resulting in the release of dye.

Example 5

Release of and Colour Reaction from Seeds Coated with WDV86-88 and WDV124 Particles A small number of coated WDV86-88 seeds were added to 0.5 ml of 50 mM sodium carbonate pH 10. A small number of WD-124 coated mung beans were added to 0.5 ml of 50× diluted Thermamyl 120 Amylase (Sigma A3404) in 5 mM TRIS/HCl pH 8. Thermamyl is a commercially available Amylase that is able to decompose starch-based particles (resulting in the release of the incorporated active compound). Control experiments were carried out by adding coated mung beans to the same buffer, thereby omitting the Thermamyl. The presence of phenolphthalein was illustrated by the solution turning pink.

FIG. 5 illustrates (i) the difference between coated and uncoated mung beans, and (ii) the difference in release of Xylenol orange by the presence or absence of Amylase.

It is obvious that Xylenol was only released in solution if Amylase is present (which degrades the BioSwitch matrix, and thereby releases the dye).

In the absence of Amylase, the BioSwitch matrix was not decomposed. Nevertheless, the Xylenol orange could be detected in the test tube. In contrast to the experiment with Amylase, the absence of Amylase led to the observation of local coloured spots: intact BioSwitch particles containing Xylenol orange. Hence, the dye was not released, but stayed associated firmly to the BioSwitch matrix.

Example 6

Incorporation of Laccase into WDV124 Gel Particles

Batch 1: Approximately 200 mg of WDV124 gel particles were allowed to swell under stirring in 30 ml 50 mM Bis-TRIS pH 6.8, for 1 hour. Subsequently, 10 ml of purified Laccase was added, the pH was re-adjusted tot 6.8, and the enzyme was allowed to be absorbed by the gel particles under stirring for 30 mM. The gel particles were was once with the same 50 mM BisTRIS buffer and harvested by centrifugation (5 min 3700 rpm). Half of the gel particles were left standing to dry on the air (30° C.), the other half was lyophilized.

Batch 2: Gel particles were grinded by means of a Retsch, until approx. 80% of the particles was able to pass a 0.05 mm sieve (code of the gel: WDV124XT: extra fine). Salt was removed from 50 ml of Laccase in 20 mM Bis-TRIS pH 6.5, by using a 200 ml Sephadex G25 column on a FPLC system. The desalted Laccase was collected in 70 ml buffer and filtrated through a 0.22 Mm sterile filter. 250 mg of WDV124XG particles was allowed to swell under stirring in 30 ml demi, for 30 min, after which 15 ml of ~1.5 mg/ml Laccase in 20 mM Bis-TRIS pH 6.5 was added. The enzyme was absorbed by the gel during 30 min of stirring. The resulting gel was lyophilized, resulting in a fine white powder.

Example 7

Coating of Mung Beans with Laccase-Containing WDV124(XF) Gel Particles

20 Mung beans were moisturized with 200 mL 2% solution of gelatinized starch. 5 mg of dry gel particles (WDV124 (XF)) were added, thereby aiming at a uniform distribution of the gel particles over the seeds (approx. 0.4 mg of particles per bean). This was achieved by shaking the seeds during addition of a household sieve. Subsequently, the coated seeds were dried by means of a blow-drier.

Example 8

Release and Detection of Laccase on Coated Mung Beans—a Two Step Reaction

To a test tube, one coated mung bean and 975 mL solution A or B (see below) was added, followed by an incubation of 10 min at ambient temperature. Thereafter, 25 Ml 5 mg/ml ABTS was added, which is oxidized by the action of Laccase, thereby changing from colourless to green. The colour reaction was followed (1-120 min) and pictures were taken a various moments in time (or the extinction of the solution was measured spectrophotometrically).

Test solution A=5 mM BisTRIS pH 6.5

Test solution B=200× diluted Thermamyl 120 Amylase (Sigma A3404) in 5 mM Bis TRIS pH 6.5

Detection of the active compound, Laccase, requires two steps: decomposition of the matrix by Amylase; followed by a colour reaction catalyzed by Laccase, thereby having ABTS to turn from colourless to green (FIG. 6). The use of exclusively Amylase or ABTS does not result in a colour development, i.e. detection of the active compound: both compounds are required.

FIG. 7 shows the colour development upon the release of the active compound from WDV124 on mung beans. This concept indicates that a two-step reaction was required for colour development. ABTS or Amylase exclusively, will not lead to a clear homogenous colour (only ABTS led to local spot of the blue/green colour: i.e. intact BioSwitch particles in which ABTS was absorbed and allowed to react with bound Laccase locally). FIG. 8 indicates that prolonged incubation with ABTS, resulted in a further development of the colour. This indicates that a relative long time was required for the development of an intense colour. Whereas the experiments described above were carried out with lyophilized BioSwitch particles, the experiments were repeated with air-dried particles (FIG. 9).

It is striking that the colour evolved much faster than in the experiments with lyophilized particles. This indicates that Laccase had lost part of its activity due to lyophilisation.

The extra fine ground particles WDV124XF were loaded with Laccase (batch 2), and similar experiments were performed (FIG. 10).

The presented results form the evidence that an optical marker system can be developed, in which two consecutive steps are required to release the colour.

Example 9

Field Test

An initial field test was carried out, using garden cress and beetroot seeds as testing material. The seeds were coated with three coating containing BioSwitch gel particles, which incorporate either Xylenol orange, Laccase or AZCL-Amylose. AZCL is commercially available as an Amylase test. It is an amylose-based substrate for Amylase; activity of Amylase leads to the released of a label from AZCL-Amylose, resulting in colour development. Uncoated seeds were used as control. Of all samples, 5×15 seeds were allowed to germinate in a mixture of potting compost, peat and (1:1:1). Germination occurred in a climate cell at 20° C. and 80% relative humidity (16 hours light/8 hours dark). Samples of the sprouted seeds were analysed immediately, or stored at −20° C.

Beetroot seeds/sprouts were analysed at: day 2; 4 and 7 (germination started from day 2-3).

Cress seeds/sprouts were analysed at; day 1; 2 and 3 (germination started from day 1). Analyses of the BioSwitch incorporated compounds, were essentially carried out as described earlier. For the field test, the analyses were downscaled to allow measurements using 96-wells microplates.

Laccase

Five cress seeds or two beetroot seeds were incubated for 20 min in buffer A or B, followed by 1 min centrifugation at 5000 rpm. 100 mL of supernatant+100 mL buffer+10 M 5 mg/ml ABTS were mixed in a 96-wells microplate, and the extinction at 405 nm was read at various time points. Measurements were carried out in duplicate, the shown results are averages of two measurements.

Xylenol Orange

Five cress seeds or two beetroot seeds were incubated for 10 min in 1 ml 5 mM TRIS/HAc buffer pH 8.0 buffer, followed by 1 min centrifugation at 5000 rpm. 250 Ml of supernatant was transferred to a microplate, and the extinction at 580 nm was read. Measurements were carried out in duplicate; the shown results are averages of two measurements.

AZCL-Amylose

Three cress seeds or 1 beetroot seed were incubated for 30 min in buffer A or B, followed by 1 min centrifugation at 5000 rpm. 250 Ml of supernatant was transferred to a microplate, and the extinction at 595 nm was read.

Measurements were carried out in duplicate; the shown results are averages of two measurements.

A field test was carried out, in order to indicate the feasibility of using optical markers system in practice. Both garden cress and beetroot seeds were coated with BioSwitch gel particles. The seeds were coated with particles, which incorporate either Xylenol orange, Laccase or AZCL-Amylose. The results are presented per active compound.

Laccase

FIG. 11 shows the results obtained with Laccase coated seeds.

The results show that the activity of Laccase could still be unambiguously detected after the seeds had been subsoiled for four days. For cress, this was the case only after 1-2 days.

Xylenol Orange

FIG. 12 shows the results obtained with Xylenol orange coated seeds.

The results show that Xylenol orange could not be detected after beet seeds been subsoiled 2 days for four days. The same held for cress after 1 day. The signal observed at day 3 for cress, is an artefact: i.e. aspecific turbidity in the measured sample.

AZCL-Amylose

FIG. 13 shows the results obtained with AZCL-Amylose coated seeds.

The results show that the presence of AZCL-Amylose could still be unambiguously detected after the beetroot seeds had been subsoiled for 2 days. After 4 and 7 days of germination, the measured values were not significantly higher than the controls, and a lot of variation in the outcomes was found. For cress, detection was still possible 1-2 days of germination.

From the results, it is obvious that the present optical marker concept based on Laccase, offered the best results. Although this concept has not been optimized, Laccase was still detectable after seeds had germinated for days.

In conclusion, it can be stated that a functional optical marker concept has been developed. The concept comprises a BioSwitch matrix, a marker compound and a release mechanism coupled to detection of the compound. As a marker compound, e.g. an enzyme, a substrate of an enzyme, or a fluorescent of coloured compound can be used. The release and detection could be performed in a two-step reaction, which minimizes the threat of false imitations. The concept enables marking of individual seeds. As indicated by an initial field test, detection of the marker compound could be performed after coated seeds had germinated subsoiled for a certain period. Interestingly, the concept allows the use of various markers. This allows end-user to apply different combinations of markers to specifically label seeds e.g. from a certain land aerial, a certain seed type or a certain harvest. Furthermore, different labels can be used by different users to mark their own seeds.

The invention claimed is:

1. Method for marking seeds comprising:

applying to said seeds a microparticle comprising a cross-linked polymer and a marker component, selected from the group consisting of a dye, an enzyme incapable of degrading the polymer of the microparticle, chemical compounds such as pH indicators, and mixtures thereof, wherein the release of said marker component from said microparticle is triggered by contact of the microparticle with an external stimulus and wherein said polymer is a carbohydrate or a protein.

2. Method for marking seeds comprising:

applying to said seeds a microparticle comprising a cross-linked polymer and a marker component, selected from the group consisting of a dye, an enzyme incapable of degrading the polymer of the microparticle, chemical compounds such as pH indicators, and mixtures thereof, wherein the release of said marker component from said microparticle is triggered by contact of the microparticle with an external stimulus and wherein said polymer is a carbohydrate or a protein, and the polymer is charged.

3. Method according to claim 1, wherein the external stimulus is an enzyme which is able to degrade the polymer.

4. Method according to claim 1, wherein the release of the marker component is induced by change of electrostatic interaction, caused by e.g. a change in the pH, a change in the temperature or a change in the salt concentration.

5. Method according to claim 1, wherein the polymer is chosen from the group consisting of starch or a derivative of starch, cellulose or a derivative of cellulose, pectin or a derivative of pectin, and gelatine or a derivative of gelatine.

6. Method according to claim 1, wherein the cross linker is chosen from the group consisting of divinyl sulphone, epichlorohydrin, a di-epoxide such as glycerol diglycidyl ether or butanedioldiglycidyl ether, sodium trimetaphosphate and adipic acid, or derivatives thereof.

7. Method according to claim 1, wherein the polymer is cross-linked by means of a cross-linking enzyme chosen from the group consisting of peroxidases, laccases, polyphenol oxidases, transglutaminases, protein disulfide isomerases, sulfhydryl oxidases, lysyl oxidases and lipoxygenases, or by a chemical cross-linking agent.

8. Method according to claim 1, wherein the enzyme is laccase.

9. Method according to claim 1, wherein the polymer is charged.

10. Method for the identification of seeds comprising the steps of:

a. marking the seeds with a method according to claim 1;

b. identifying said seeds by applying an appropriate external stimulus to release the marker component from said microparticle; and c. assaying for the marker component.

* * * * *

UNITED STATES PATENT AND TRADEMARK OFFICE

CERTIFICATE OF CORRECTION

PATENT NO. : 8,431,375 B2
APPLICATION NO. : 12/667963
DATED : April 30, 2013
INVENTOR(S) : Happe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 613 days.

Signed and Sealed this
Eighth Day of September, 2015

Michelle K. Lee
*Director of the United States Patent and Trademark Office*